US005681749A

United States Patent [19]
Ramamoorthy

[11] Patent Number: 5,681,749
[45] Date of Patent: Oct. 28, 1997

[54] CONTROLLING ACID CONCENTRATION IN A HYDROCARBON PROCESS

[75] Inventor: Periaswamy Ramamoorthy, El Sobrante, Calif.

[73] Assignee: Chevron U.S.A. Inc., San Francisco, Calif.

[21] Appl. No.: 483,631

[22] Filed: Jun. 7, 1995

Related U.S. Application Data

[63] Continuation-in-part of Ser. No. 278,348, Jul. 21, 1994, abandoned, which is a continuation of Ser. No. 858,795, Mar. 27, 1992, abandoned.

[51] Int. Cl.$^6$ ................................................ G01N 21/00
[52] U.S. Cl. ........................ 436/55; 436/150; 436/171; 436/173
[58] Field of Search ................................ 436/51, 55, 150, 436/171, 173; 422/82.01, 108

[56] References Cited

U.S. PATENT DOCUMENTS

| 3,607,087 | 9/1971 | Graham | 422/224 |
| 3,653,835 | 4/1972 | Brandel | 436/100 |

*Primary Examiner*—Lyle A. Alexander
*Attorney, Agent, or Firm*—V. J. Cavalieri; T. J. Hadlock

[57] ABSTRACT

A method is disclosed for determining the acid concentration in acid-water-hydrocarbon (acid-soluble oil) solutions using near-infrared spectrophotometry. The use of a multivariate analysis such as Partial Least Squares algorithm enables one to predict simultaneously the concentrations of water and acid-soluble oil in the process acids from the near-infrared spectra. Although the preferred embodiment is directed to sulfuric and hydrofluoric acids used for alkylation, the method is also applicable to processes using other organic or inorganic acids containing hydrogen bound to either carbon, oxygen or nitrogen. Advantages are elimination of acid waste, hazardous acid handling, and better alkylate product quality.

20 Claims, 12 Drawing Sheets

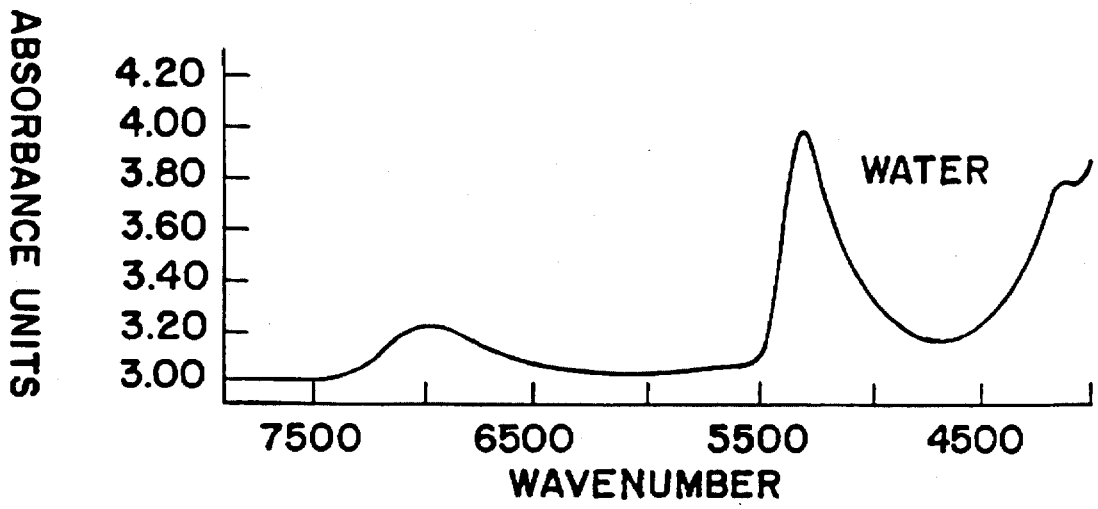
FIG_3a
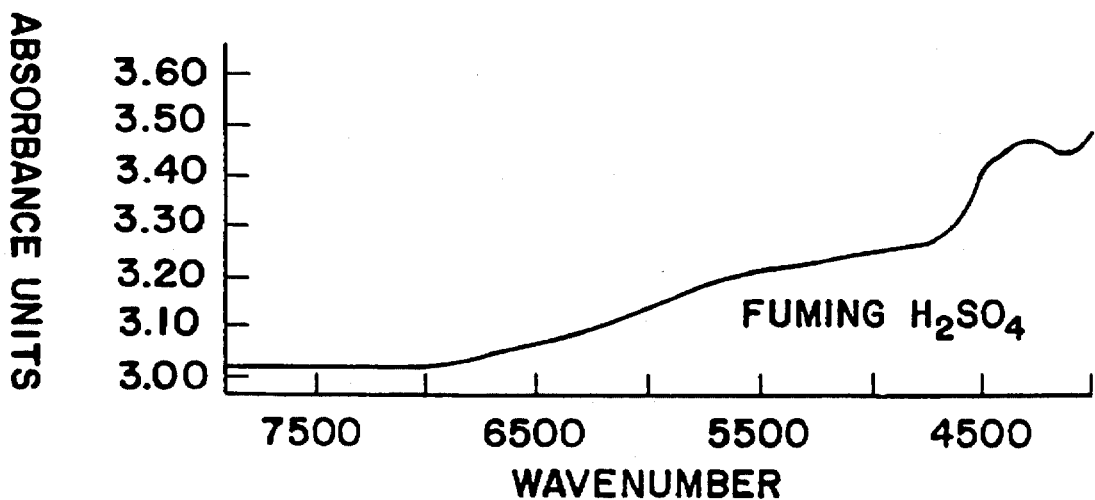
FIG_3b

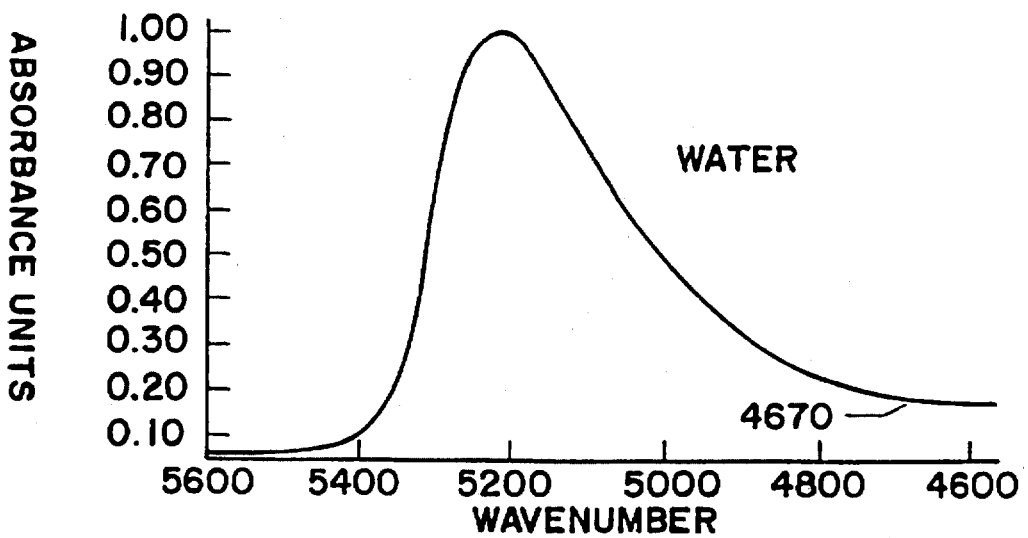
FIG_4a
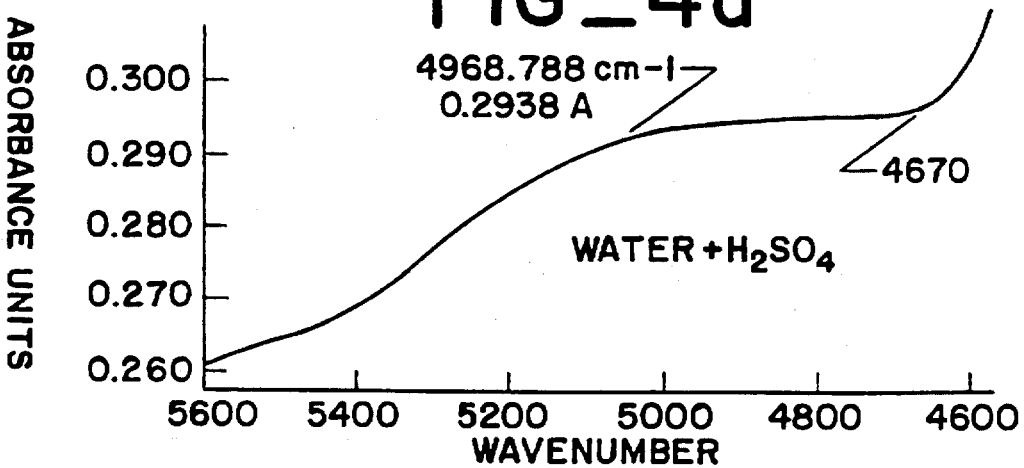
FIG_4b
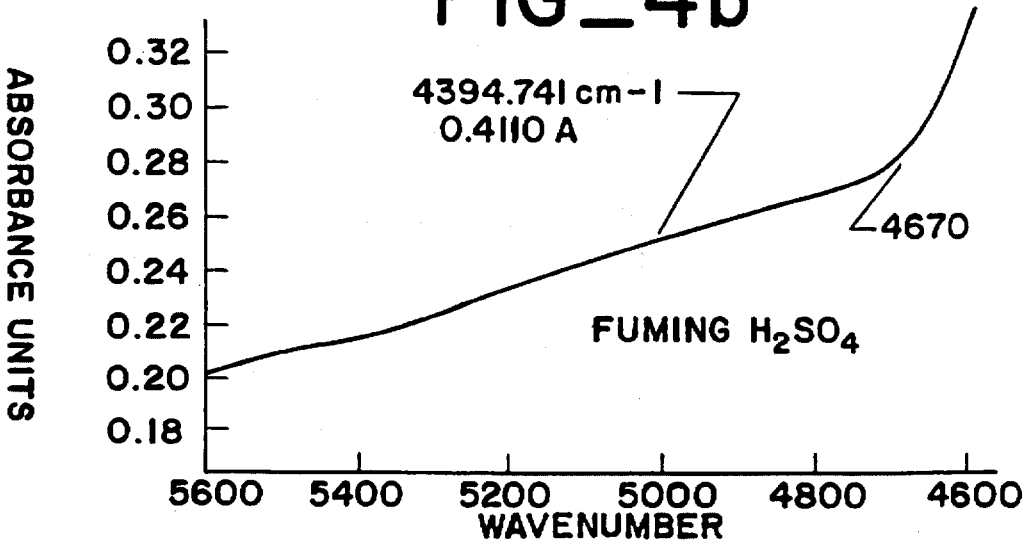
FIG_4c

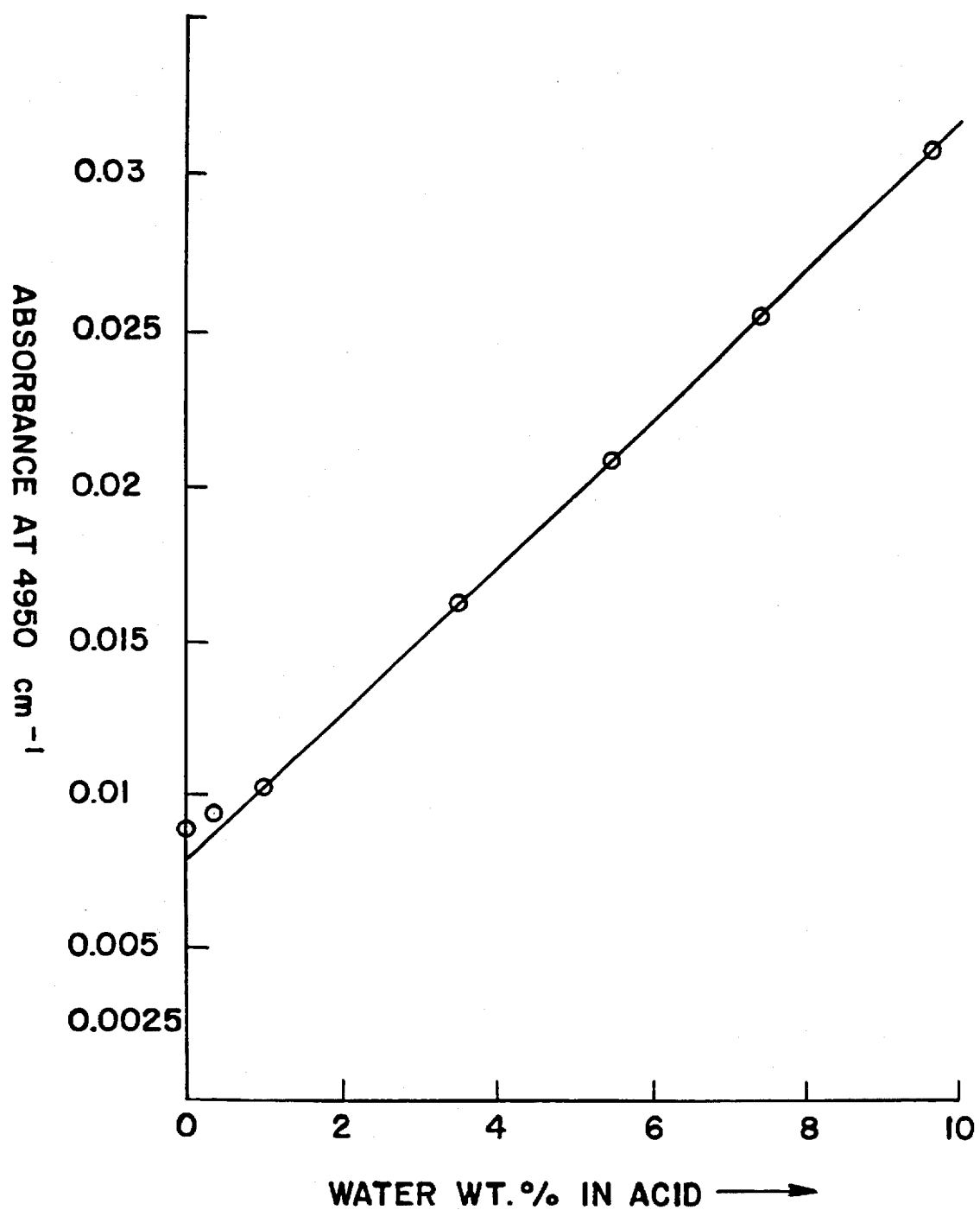
FIG_5

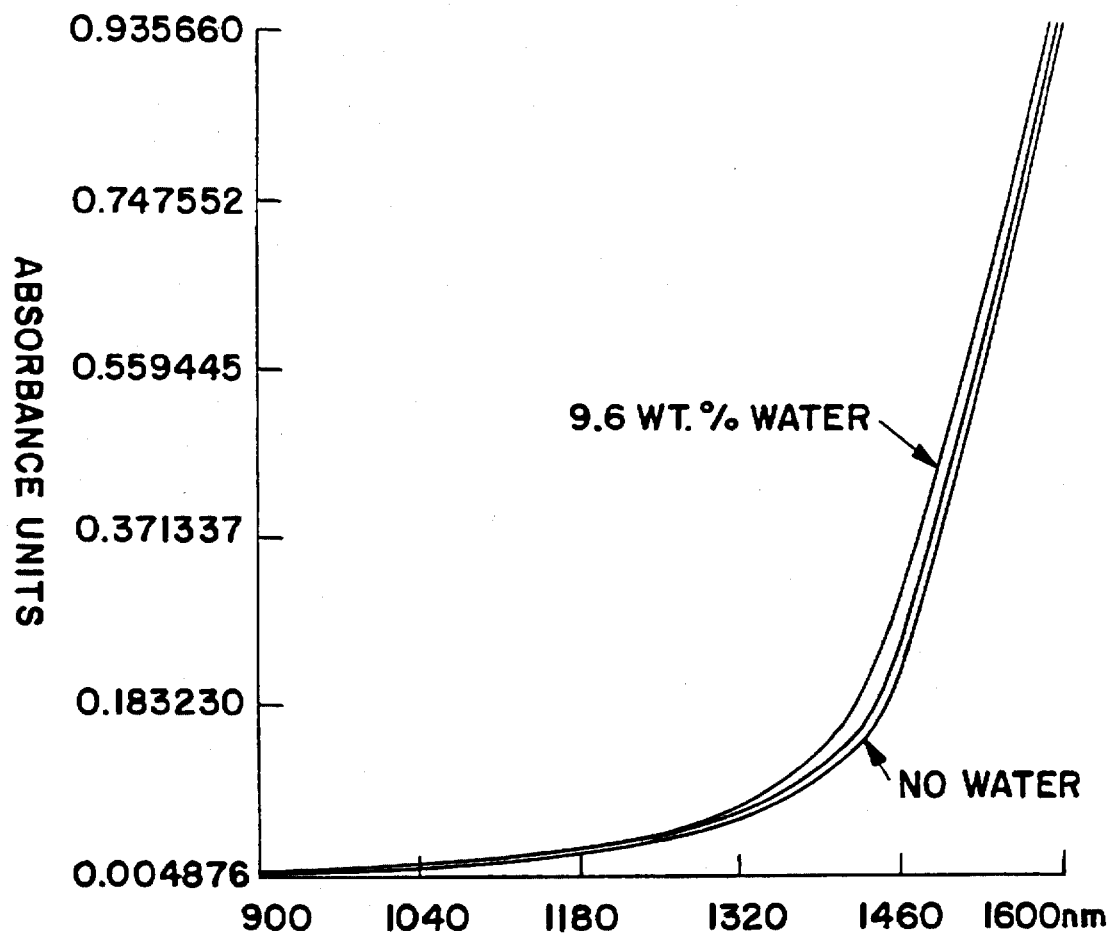
FIG_6

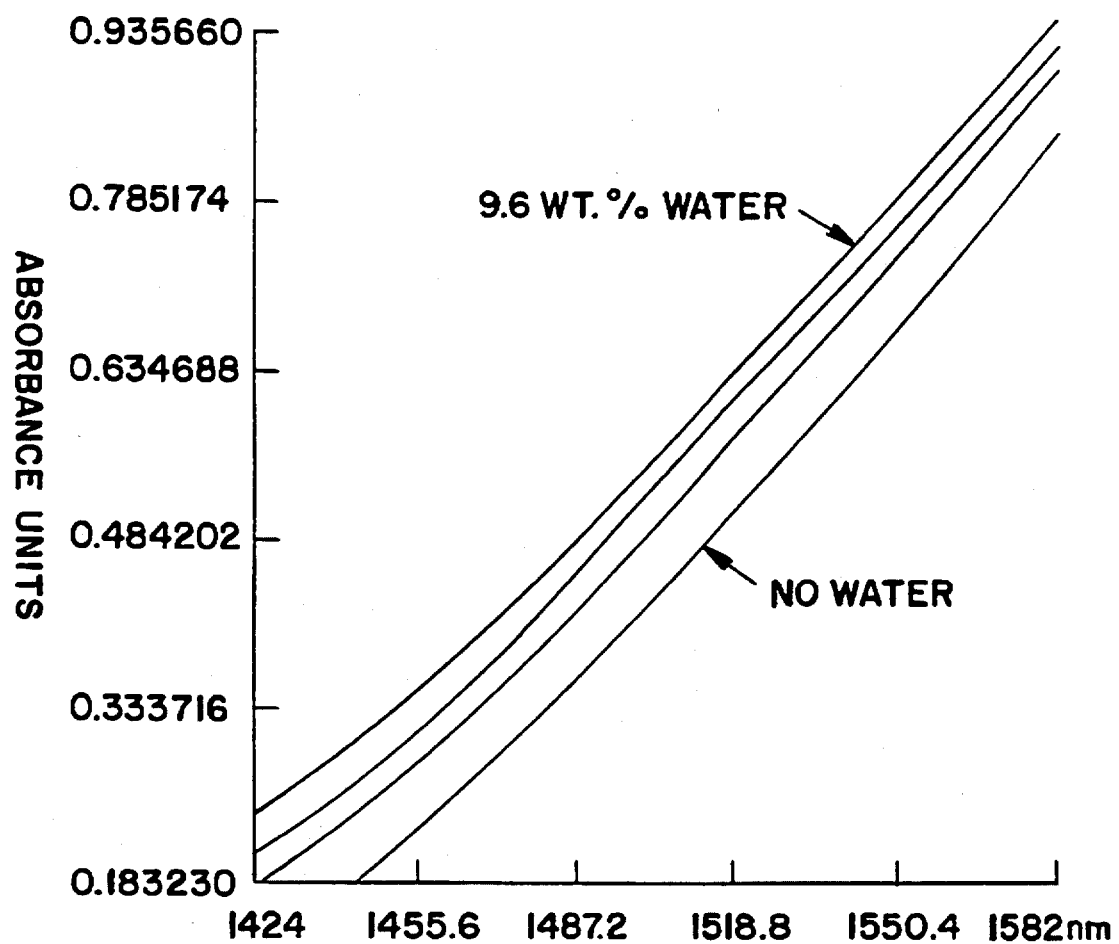
FIG_7

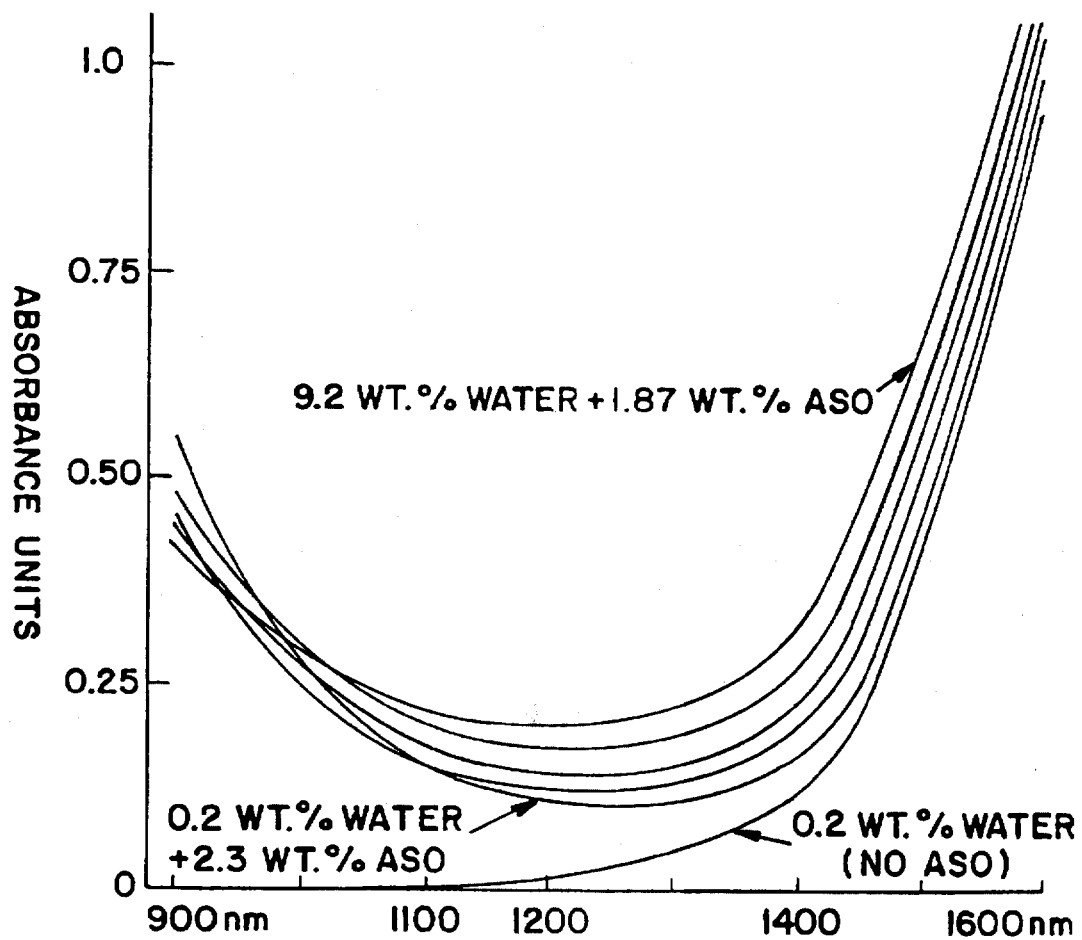
FIG_8

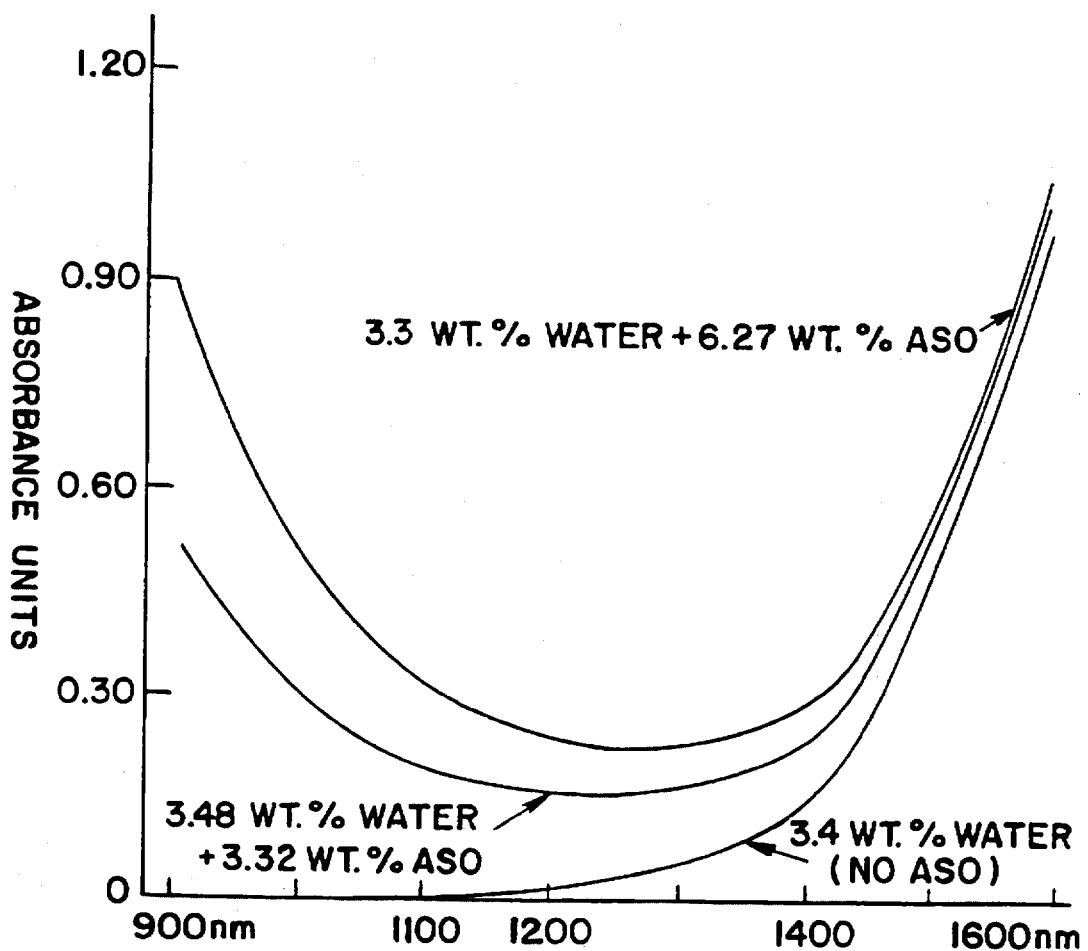
FIG_9

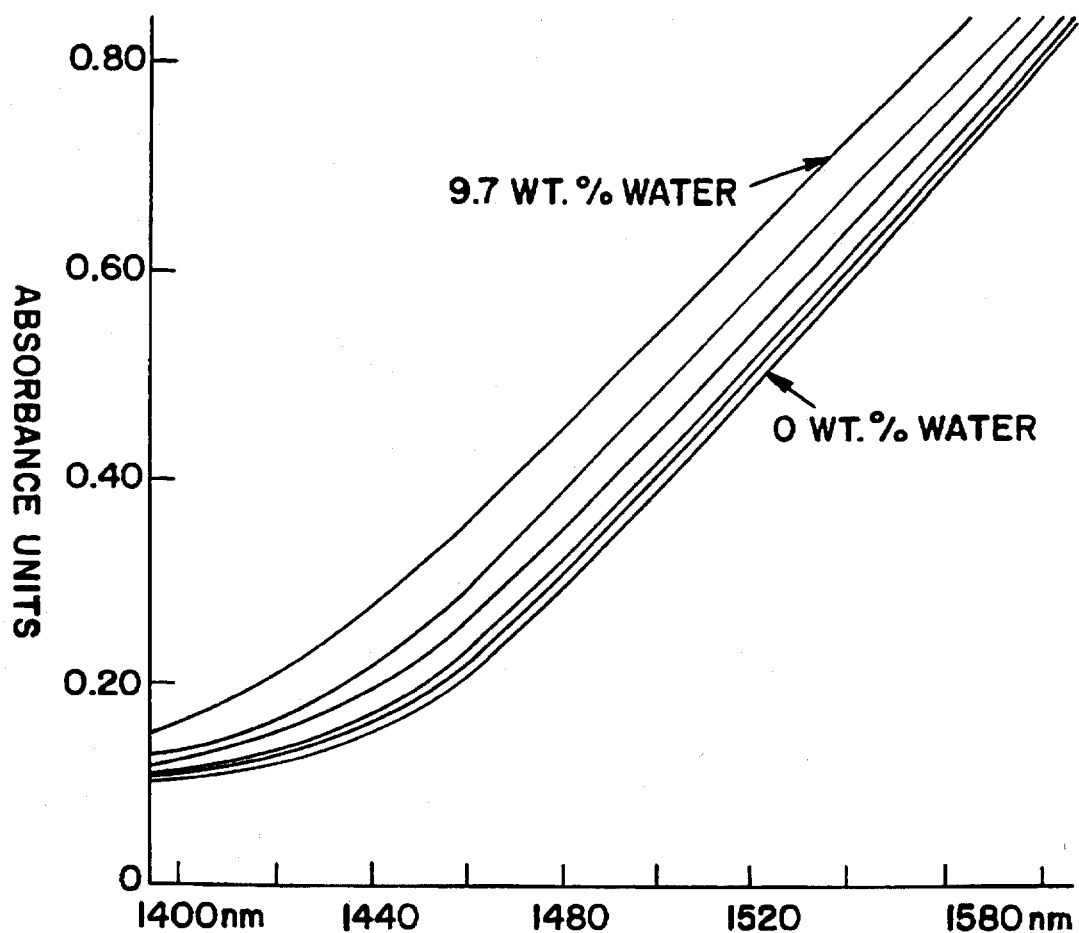
FIG_10

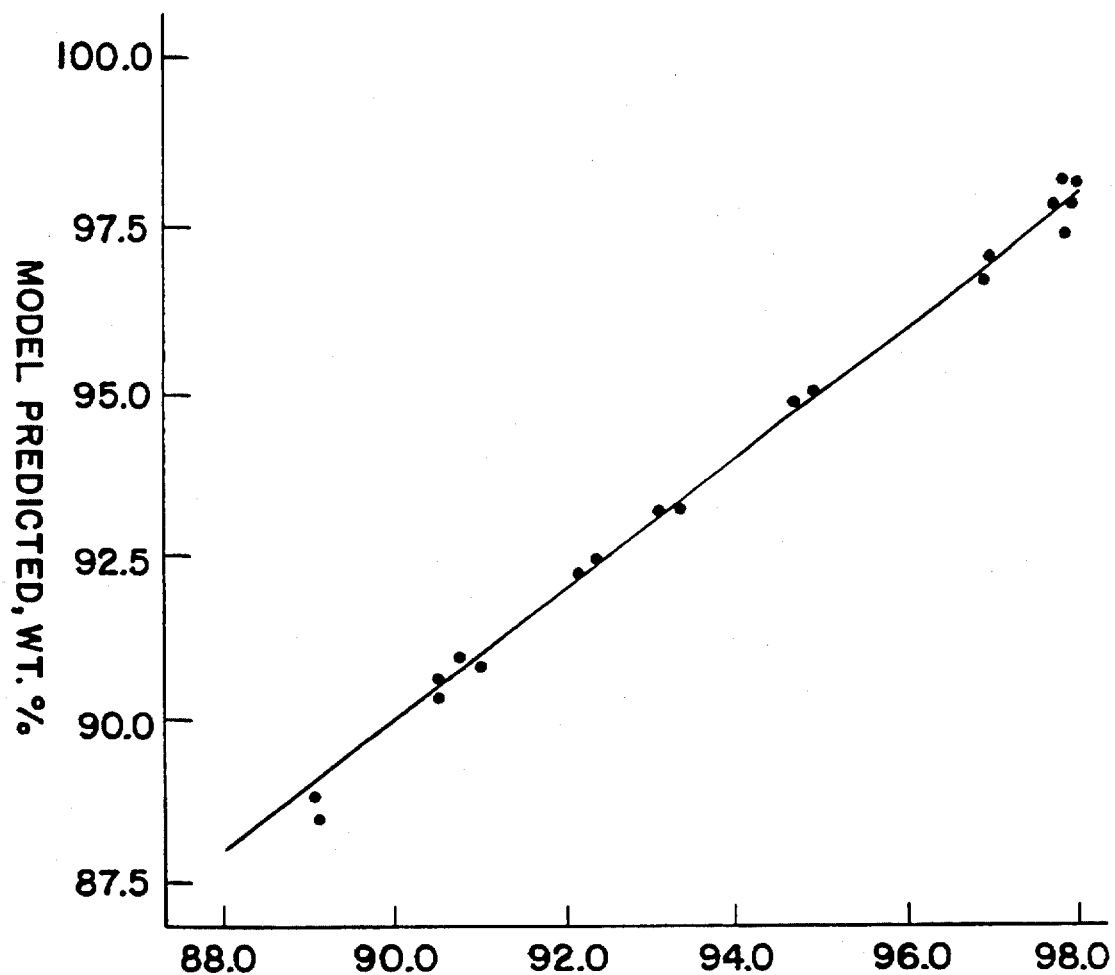
FIG_11

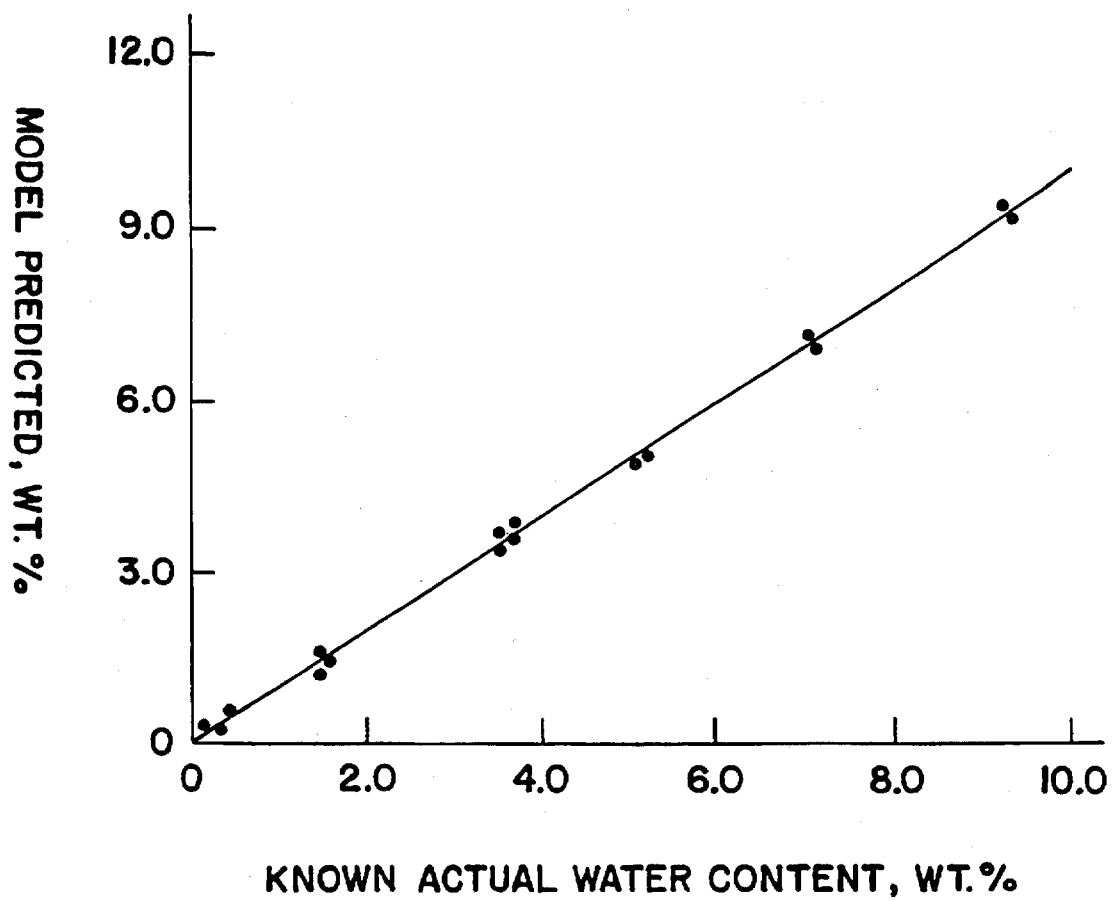
FIG_12

CONTROLLING ACID CONCENTRATION IN A HYDROCARBON PROCESS

This application is a Continuation-in-Part of U.S. Ser. No. 08/278,348, filed Jul. 21, 1994 now abandoned, which in turn is a Continuation of U.S. Ser. No. 07/858,795, filed Mar. 27, 1992, now abandoned.

FIELD OF INVENTION

The present invention concerns the determination and control of acid concentration in acid-water solutions containing, in addition, an acid soluble oil. More specifically, one embodiment of this invention relates to an improved method for the determination of acid strength in a hydrocarbon refinery alkylation process using near-infrared spectroscopy and a multivariate mathematical analysis for controlling the acid catalyst strength to improve the alkylation process.

BACKGROUND OF THE INVENTION

Refiners alkylate olefinic hydrocarbons with isoparaffins to produce highly branched, paraffinic hydrocarbons called motor alkylate. Branched aliphatic hydrocarbons are important constituents of automotive and aviation fuels because of their high octane ratings and relatively low volatility. The olefinic hydrocarbon feed generally comes from a catalytic cracker and contains olefins, paraffins, and isoparaffins in the carbon number range $C_3$–$C_5$. Common impurities present in the feed are mercaptan sulfur, diolefins, and free water. Sometimes the butane-butene stream containing isobutylene is used for methyl tertiary butyl ether (MTBE) production, and the $C_4$ raffinate from the MTBE unit is sent to an alkylation plant. In the MTBE unit certain oxygenated compounds such as dimethyl ether and methanol may become additional impurities in the feed to the alkylation unit. Diolefins such as butadiene present in the butane-butylene stream are known to consume the acid catalyst used in commercial alkylation units at a rapid rate resulting in the formation of polymeric oil in the acid phase and lowering the alkylate octane. The diolefin content of the butane feed runs high at about 1–2% when, for example, the catalytic cracking unit runs high-octane catalysts or at high severity, for example, high riser outlet temperature. Oxygenated compounds and the free water often also present in the feed to the alkylation unit tend to dilute the acid catalyst during the course of reaction and also result in lowering the alkylate product quality. Further, water that may be formed as a result of possible side reactions in the alkylation unit reactor or settler also tends to dilute the acid catalyst and lower the product alkylate octane.

The effect of acid strength on the octane number of the product alkylate has been documented. For example, Albright and coworkers showed in a series of bench scale laboratory tests that the octane number of the product alkylate depended upon both the water and acid-soluble oil concentrations of the acid catalyst. (L. E. Albright, L. Houle, A. M. Sumutka, and R. E. Eckert, Ind. Eng. Chem. Process Des. Develop., Vol. 11 (No. 3), pages 446–450, 1972). It is known that alkylate product improves by about a whole octane number if the water content of the acid is lowered from 3 to 2 weight percent at a constant red oil (defined herein below) content of about 5 weight percent.

Acid-Soluble Oil

In the course of the alkylation reactions involving olefins, the acid catalyst often becomes contaminated with a polymeric organic contaminant, also known as "red oil" or acid-soluble hydrocarbon. Red oil is a complex mixture, the exact composition of which is not precisely known. Red oil is believed to be a product of the alkylation reactions involving hydrogen transfer. Red oil is also variously referred to as "acid oil", "polymeric oil", "acid soluble sludge", or "conjunct polymer". As polymeric oil accumulates in the acid phase, the acid strength of the catalyst is lowered, thus impairing the catalyst activity.

The composition of red oil in an alkylation unit varies depending upon the feed composition and reaction conditions. The polymeric organic contaminant is soluble in the acid catalyst and may be chemically bound by strong sulfuric acid. Red oil's solubility in the acid decreases at lower acid strength and becomes nearly insoluble in the acid when the acid is diluted with water to less than about 50 weight percent acid.

The water content of the acid catalyst controls the ionization level in the acid phase. The water content generally varies from about 2 to 5 weight percent and the acid soluble hydrocarbons vary from about 4 to 7 weight percent.

Removal of Acid-Soluble Oil

For commercial locations where the fresh acid supply is located far from the refinery, the cost of fresh acid or transportation of spent acid for regeneration can be quite significant. In commercial operation, the polymeric oil contaminant is typically eliminated from the alkylation system by withdrawing the acid of about 85 to 92 weight percent concentration as "spent acid" from the alkylation system and replenishing the system with fresh acid of about 98 to 99.9 weight percent acid. Since the polymeric organic contaminant amounts to only about 3 to 8 weight percent of the spent acid, prior to my present invention herein described below, a large amount of acid had to be disposed of in order to eliminate a relatively small amount of the acid-soluble oil from the system.

The same is true for the water dilution effects. Typical water content of the alkylation acid may vary between 2 and 5 weight percent in the alkylation system. To reduce the water content of the acid from 3 to 2 weight percent, a large amount of fresh acid at 99 weight percent or higher will be required to be transported to the site, and spent acid disposed of, all at significant expense.

Acid Run-away

In the operation of commercial alkylation units, a situation of rapid fall in catalyst acidity is known in the art as "acid run-away". During the alkylation reaction, as the acid progressively becomes diluted with unsaturated polymers, tert-butyl cations, sulfate esters, and other impurities the acid catalyst will sometimes, without warning, rapidly drop in acidity. The acid run-away scenario also depends to some degree upon a set of alkylation conditions: chiller temperature, hydrocarbon-to-acid ratio, sulfur and butadiene contents of the feed, and other related plant factors, which are not always easily predicted. For a set of alkylation conditions, there is a minimum alkylation acidity that refiners use in practice. If the acidity of the system acid drops below this predetermined figure, the alkylation reaction ceases and the acid strength of the acid drops even more rapidly.

If an acid run-away is not detected immediately, the acidity will drop so fast and so low that the entire acid inventory of the plant is made inactive and must be removed. In addition, during acid run-away, the product alkylate usually becomes contaminated with sulfur compounds in the form of alkyl sulfates having a negative or reduced lead susceptibility. When such a condition occurs, both the acid and the valuable product alkylate must be discarded or reprocessed at great expense.

Acid run-aways are also known to occur more often with propylene-rich feed using sulfuric acid as the catalyst than with butylene-rich feeds. It does not mean that acid runaways do not occur with butylene-rich feeds. There are instances of acid run-aways noted in the case of butylene-rich feeds. In general, commercial alkylation plants operate with a used or spent acid discharge acidity of about 90 weight percent because the operators believe that it is about the minimum safe acidity. However, some operators are known to run at acidities lower than 90 weight percent. Hughes et al. describe butylene alkylation operation at 85 weight percent acidity with an acid consumption of about 0.6 pound acid per gallon of alkylate and at 92 weight percent acidity with about 1.2 pound of acid consumption per gallon of alkylate. (Hughes, E. C., et al. Ind. Eng. Chem., Vol. 43, No. 6, pp. 1447–1451, 1951.)

It is advantageous to operate the alkylation plant with the alkylation acid as close to the minimum acidity as possible since this type of operation results in the lowest acid consumption. However, some alkylation plant operators believe that running in such a manner tends to promote corrosion, and also tends to result in more acid run-aways. As a result, many operators try to run at an acidity level that is slightly above the minimum for their alkylation system acid. For example, acidities of about 90–92 weight percent rather than 88–90 weight percent acid are commonly used. It is indeed clear that accurate monitoring and control is vital to successful operation of a commercial alkylation unit.

If an unusually rapid drop in acidity is detected before the acidity drops below the safe minimum acidity, the acidity can usually be brought back to a safe level by increasing the fresh acid feed and/or by decreasing or cutting out the olefin feed. A major difficulty in present commercial operation is that a few hours may elapse before an acid sample is taken, analyzed, and acidity data are obtained. Operators, prior to my present invention, when forced to rely on a chemical laboratory for acid titration data to determine acid catalyst strength, are left to operate the plant without acid-strength data while the laboratory is closed during nights and weekends. When test results are finally obtained, the alkylation system acidity may be already so low, for example, 80 weight percent, the alkylation acid is no longer active for alkylation reaction. The result is that no matter how much fresh acid is charged to the system, and even with the fresh olefin feed curtailed, the acidity cannot be raised to a point at which the acid will again act as the alkylation catalyst. The operator is usually left to remove the acid inventory from the system.

It is for the above multitude of reasons, among other factors, that accurate, fast (i.e., on-line), and reliable measurement and control of alkylation acid strength becomes important. Indeed, an accurate on-line measurement of acid strength is critical to the performance of alkylation processes.

In the alkylation of isoparaffins and olefins with a strong mineral acid such as sulfuric acid, it is critically important to be able to recycle the used or spent acid back to the reactor.

This used or spent acid is comprised of three components, i.e., acid, water, and acid-soluble hydrocarbons known, sometimes, as red oil or acid-soluble oil (ASO). It is because of the complexity of this recycle acid (and, in particular, the presence of the acid-soluble oil) that others have found it difficult and time-consuming to determine the acid content of the recycle acid. It is, of course, essential to know accurately the acid content of the recycle acid in order to determine the amount of fresh acid to add to bring the mixture of fresh and recycle acid to the concentration of the acid desired in the alkylation reactor.

When absorbance of the recycle acid was measured with near-infrared (NIR) between 900 and 1600 nm, no peaks were observed at a given water or ASO content, such as shown in FIGS. 8 and 9. Only a single broad curve was observed. Such a single broad curve appears to be of no value in determining individual components, e.g., acid concentration in the recycle acid.

Spectroscopic data are generally useful due to the presence of unique peaks generated at certain wavelengths due to the presence of particular types of chemical bonds or compounds. When no peaks are observed in the spectral data, i.e., when a single broad curve is obtained, the use of the spectroscope is usually discarded.

It was also found that pure (fuming) sulfuric acid does not absorb in the NIR range between 900 and 1600 nm (see FIG. 3b). As water was added to the acid, an upward shift was noted at 1440–1460 nm (see FIG. 10). It was found, surprisingly, that each sequential addition of water generated its own unique curve (see FIG. 6). A similarly surprising phenomenon occurred upon the addition of ASO to a water-acid solution, i.e., an upward shifting of the curve as the ASO concentration increased (see FIG. 9). Fortuitously, the ASO shift occurred in the NIR 900 to 1100 nm range, i.e., it did not overlap the water shift range.

A series of runs were made at varying concentrations of red oil, water and acid to develop a family of curves, any one of which would appear to be meaningless (see FIGS. 8 and 9). The NIR curve generated by a recycle acid of unknown acid strength is then compared to the standard family of curves mathematically by an appropriate technique, such as multivariate analysis to provide the concentration of acid in the recycle acid.

The invention here is in the finding that two different and independent portions of the NIR spectra in the 900 to 1600 nm range (900 to 1100 nm for ASO and 1440 to 1460 run for water) shifted upward upon an increase in either the water or ASO content of a liquid mixture comprising a mineral acid, water and ASO. This finding allows for the generation of a family of curves any one of which would appear to be meaningless, but the use of the family of curves allows for a comparison of an NIR spectra curve in the 900 to 1600 nm range for a recycle acid of unknown acid concentration (but containing also red oil and water) so as to determine quickly and with accuracy the weight percent acid, water, and red oil in the recycle acid.

Analytical Methods

Certain methods are in present use for measurement of the acid strength and other methods are useful for the water analysis alone. The traditional methods for measuring water content in sulfuric acid are described by O. T. Fasullo in "Sulfuric Acid: Use in Handling", New York, N.Y., (McGraw-Hill Book Company, pages 192–197, 1965). These traditional methods for determining acid or water are time-consuming and labor-intensive in commercial operation. They require bleeding of the acid from the process stream creating potential environmental and acid handling problems, with the possible loss of volatile components during the acid bleed and make-up process. Furthermore, previous methods employed by others are not responsive to relatively short-swing upsets in the operation. Alkylation plant operators could not, prior to this invention, adequately maintain a continuous control of the acidity of the alkylation catalyst and therefore control the product octane quality.

Several attempts have been made to accurately and reliably measure the acid strength of alkylation acids on a sampling but non-continuous basis. For example, U.S. Pat. No. 3,653,835, issued Apr. 4, 1972 to A. J. Brandel teaches measuring the specific gravity of a sample of spent sulfuric acid as a means of measuring the concentration of acid (Column 1, lines 14–16).

Brandel teaches in Column 1, lines 58 et seq, that "Heretofore, the acidity of the alkylation acid could be determined spectrophotometrically, but this technique suffers from several disadvantages . . . ". One of the "disadvantages" was a requirement for the "continuous addition of an indicator compound such as alizarin blue in known amounts to the sample. Accordingly, a complicated and expensive control and metering system for the indicator compound is needed." (Emphasis added.)

Brandel further teaches that a sample is removed from the system and fed into the apparatus shown in FIG. 2 of Brandel. Further, Brandel teaches in Column 3, lines 73 et seq, that "volatile and high molecular weight hydrocarbons must be removed from the sample if the gravity determinations are to have any reproducible significance". (Emphasis added.) These high molecular weight hydrocarbons constitute, of course, the red oil. Thus, Brandel's teachings are not applicable to in-line measurements of recycle acid in the conjoint presence of acid, water and red oil.

Similarly, Brandel's teachings regarding the prior use of spectrophotometry would suggest the same separation of a sample, removal of red oil, and the separate addition of a dye. Thus, Brandel's teachings regarding spectrophotometry are not applicable to the NIR in-line technique of the present invention which determines the concentration of acid, water and acid-soluble oil in their conjoint presence.

In addition, if one with ordinary skill in the art were to use Brandel's spectrophotometer in-line, the entire system would be contaminated with the dye and "known" quantities of the dye in any given sample would be meaningless. Thus, the teachings of Brandel would, if anything, lead one with ordinary skill away from the use of spectrophotometers for in-line continuous measurement of the acid concentration in recycle acids. In accordance with this invention, continuous in-line measurement of acid concentration in the conjoint presence of water, acid and red oil is possible using NIR spectra in combination with an appropriate multivariate analysis.

U.S. Pat. No. 3,935,097, issued Jan. 27, 1976 to Roof, describes a system directed to the high pressure liquid chromatographic separation of hydrofluoric acid and water. U.S. Pat. No. 3,478,125, issued Nov. 11, 1969 to Chapman, is directed to a method for the acid strength control of the hydrofluoric acid based alkylation process. U.S. Pat. No. 4,016,074, issued Apr. 5, 1977 to Porter, describes a separation and control process using chromatography similar to the process of Roof. U.S. Pat. No. 4,009,998, issued Mar. 1, 1977 to Benningfield Jr., discloses a method for measuring the concentration of hydrofluoric acid by electrical conductivity means. All of these methods are based on sampling. Prior to this invention, there is no description of a continuous on-line analysis of acid strength in an alkylation process in the conjoint presence of acid, water and red oil.

Some operators have used the viscosity of the spent acid to correlate the acidity of the system acid. However, the devices based on viscosity have seen limited success primarily because they use an indirect means to correlate the acidity. Viscosity-based devices also require considerable maintenance. Furthermore, the presence of red oil in varying amounts can adversely influence the viscosity correlation.

Previous attempts to measure acid strength in the sulfuric acid based alkylation process did not yield a satisfactory correlation. For example, the electrical conductivity of the sulfuric acid-water solutions is highly nonlinear. But over a narrow range of 98–100 weight percent sulfuric acid, the solution conductivity seems to vary linearly with the acid concentration. However, the presence of an acid-soluble oil in the acid catalyst drastically affects the limited range of linear relation between the acid strength and the electrical conductivity. The NIR technique of this invention used with an appropriate multivariate analysis is the first time on-line continuous analysis of sulfuric acid concentration in the conjoint presence of water and red oil has been achieved.

Other methods have been employed in an attempt to achieve in-situ determination of the acidity of acid-water solutions. For example, on-line continuous acidity analysis can be accomplished by monitoring velocity of sound in the flowing acid stream. The velocity of sound in any medium is known to depend upon the density of the medium. However, this correlation is accurate only for certain acid-water solutions that do not contain acid-soluble oil.

The apparatus and methods of all the above attempts to reliably and accurately measure the acidity of the alkylation acid fall short of meeting an operator's need to accurately monitor and control the acid strength in commercial operation. In a commercial plant, the amount of acid-soluble oil content of the acid may vary over a wide range. Therefore, it is desirable to have a method that can reliably measure the acid strength regardless of the temporary swings in the acid-soluble oil content. Even with attempts by other methods to remove the "red oil" and hydrocarbons from the acid catalyst prior to attempting measurement, operators of alkylation reactors remained uncertain of the acid catalyst strength as measured by unreliable devices and methods, thus tending to more cautiously choose to purge and replace the system acid with expensive make-up acid.

Most importantly, prior to my present invention, the operator has been unable to continuously monitor on-line and control with confidence the acid strength in a commercial hydrocarbon conversion process.

It is an object of my invention to provide a reliable method of measuring the acid strength in a mixture comprising a mineral acid, water and red oil in a hydrocarbon conversion process by a continuous in-line technique to enable operators to make adjustments to their fresh acid addition rate and spent acid purging rate, thereby improving product quality.

An improved apparatus and method for accurate determination of acid strength in hydrocarbon conversion processes is much desired.

BRIEF DESCRIPTION OF THE DRAWINGS

FIGS. 3a and 3b are Mattson spectra of water and fuming sulfuric acid, respectively.

FIGS. 4a, 4b and 4c are Mattson spectra of water and fuming sulfuric acid in a narrow waveband with the dilution effect of water depicted.

FIG. 5 is a graphical representation of the absorbance vs. water content of sulfuric acid.

FIG. 6 depicts the near IR spectra from various concentrations of acid-water solution in the 900–1600 range, using a fiber optical device of a Guided Wave Model 300 analyzer and a 2 mm path length.

FIG. 7 depicts the same spectra data as FIG. 6 detailing the range of interest, 1424–1582 nm.

FIG. 8 depicts the effect of water concentration in water-acid-oil solutions on the near-infrared spectra.

FIG. 9 depicts the effect of acid-soluble oil content for solutions with greater oil concentration.

FIG. 10 depicts the absorbance spectra in the narrow range of 1400 to 1580 nm for $H_2SO_4$ at various water concentrations.

FIG. 11 displays the predicted acid strength versus actual acid strength.

FIG. 12 displays the predicted water content versus actual water content for various wt. % water solutions.

SUMMARY OF THE INVENTION

Figure 1:
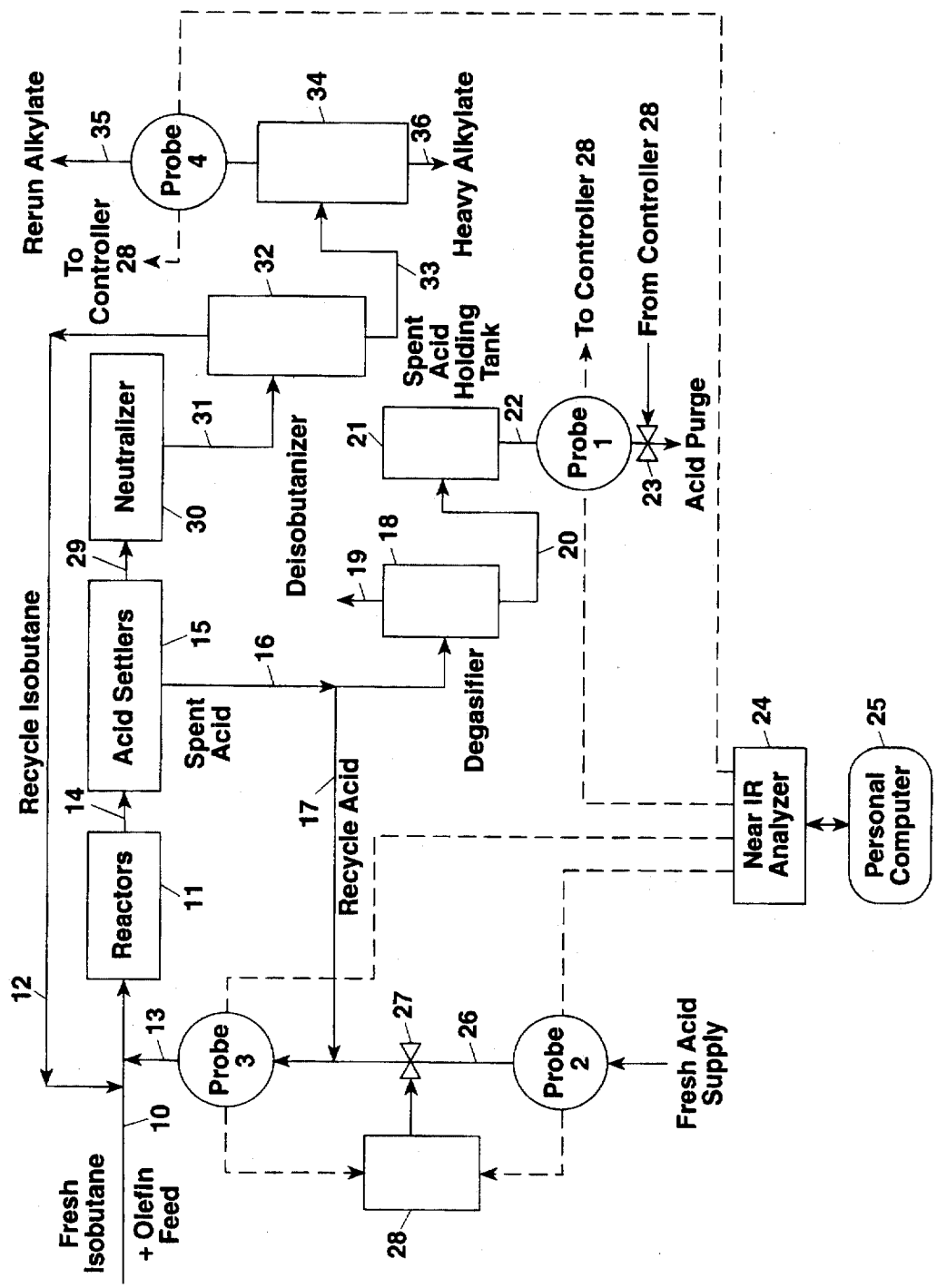
FIG. 1 is a schematic view of the alkylation process preferred embodiment with major system components depicted.

The present invention resides in the use of near-infrared (NIR) spectroscopy for determining the concentration of mineral acid in a mixture comprising mineral acid, water and acid-soluble hydrocarbons.

In one aspect of this invention, the determination of the concentration of mineral acid occurs using the NIR spectroscopic absorbance data and a multivariate analysis, such as a Partial Least Squares algorithm.

In yet another aspect, the present invention relates to a process for controlling the acid strength in a hydrocarbon conversion process comprising the steps of contacting a hydrocarbon stream with a catalytic solution comprising an acid under hydrocarbon conversion conditions, spectrophotometrically generating absorbance data of the solution, determining the solution acid concentration using multivariate analysis and the absorbance data, and adjusting the concentration of the acid to a predetermined range.

In the preferred embodiment, my invention is an improved method for determining and maintaining the acid catalyst activity in the sulfuric or hydrofluoric acid catalyzed alkylation reaction.

The present invention is also applicable to other hydrocarbon processes where a liquid inorganic acid is used as the main catalyst or as a co-catalyst or a desirable medium to conduct the reaction and produce the desirable products, including an acid-soluble oil, i.e., a red oil. Examples of such other hydrocarbon processes are production of isopropyl alcohol from olefins using phosphoric acid catalyst over a support and selective isomerization of butylenes using phosphoric acid over a silica support.

The present invention is also a new method for on-line continuous measurement of water content in many mineral acid-water solutions containing red oil like materials including but not limited to sulfuric acid, hydrofluoric acid, and phosphoric acid.

My present invention is also useful in the continuous measurement of water-like components that are described by the near-infrared spectra as having oxygen-hydrogen bonds. Compounds containing nitrogen-hydrogen bonds can also be measured using the present invention based upon the infrared bands for the nitrogen-hydrogen bond in the near-infrared spectrum, for example one of the bands at 1460 nanometers wavelength. My present invention may also be applied to processes where the hydrocarbon content of the process acid needs to be measured and controlled. This is made possible by the infrared absorption band due to carbon-hydrogen bonds present in the acid.

My present invention utilizes spectroscopy in the near-infrared or "NIR" range of from about 700 nanometers to about 2500 nanometers wavelength and multivariate analysis techniques to achieve an accurate and reliable determination of acid strength. In a preferred embodiment, the multivariate analysis technique for interpreting the NIR data is Partial Least Squares or Prediction of Latent Structures (PLS).

Among other factors, I have found the addition of acid-soluble oil (ASO) to a liquid inorganic acid-water solution (simulating recycle sulfuric acid from an isoparaffin-olefin alkylation reaction) generates a separate unique curve for each change in ASO concentration so that a family of curves can be generated (as shown, for example, in FIG. 8) in the near-infrared absorbance spectrum. Similarly, the addition of water to a liquid inorganic acid-ASO solution generates a separate unique curve for each change in water concentration so that a family of curves can be generated (as shown, for example, in FIG. 9) in the near-infrared absorbance spectrum. Recycle acid from an alkylation process containing an unknown acid concentration will generate its own unique curve in the near-infrared range. For example, the near-infrared band in the range 900–1600 nm can be passed through the alkylation acid containing the red oil and water through a two millimeter path. The strong O—H stretch first overtone band at 1440–1460 nm can be used to determine the water content. The red oil present in the alkylation acid absorbs in the range 900–1100 nm and does not apparently interfere with the water absorption near 1440–1460 nm. Therefore, the hydrocarbon absorption band in the range 900–1100 nm can be used to determine the red oil content in the presence of water and mineral acid.

Surprisingly, interactions among the red oil, water and the acid that appear to be significant during spectroscopy may be dealt with in accordance with my invention. I have discovered that any spectral changes that occur due to the red oil's presence can be treated mathematically by the Partial Least Squares or Principal Component Regression methods which methods mathematically compares the curve generated by the recycle acid of unknown concentration with the family of standard curves in its data bank, including interpolation between the curves. The use in the preferred embodiment of Partial Least Squares enables one to relate the near-infrared spectra of the acid catalyst containing both water and the acid-soluble oil to the concentrations of both water and the red oil, allowing the prediction of each individually. The acid concentrations can then be determined by difference.

In one embodiment of the process of the present invention, the predicted concentration of the acid is monitored in accordance with the hereinafter described devices and analytical techniques, and when the predicted acid concentration reaches a predetermined level, a measured amount of spent acid is removed from the alkylation system and a measured amount of fresh acid added, in order to maintain a desired alkylation acid strength. In this way, the concentration of acid catalyst is continuously controlled, and the octane value of the product alkylate may be maximized.

In a preferred embodiment of the present invention, a set of cladded optical fiber waveguides is employed in the transmission of near-infrared energy between a measurement device or an analyzer and the liquid acid stream. In yet another embodiment of the present invention, oleum is added to the alkylation acid based upon the solution strength as measured, to maintain a desired acid catalyst strength in the alkylation process.

DETAILED DESCRIPTION

The Hydrocarbon Process

In a preferred embodiment, the hydrocarbon process to which the present invention applies is alkylation. The major processing steps of a commercial alkylation unit, and also various preferred monitoring points for the practice of this embodiment are outlined in FIG. 1.

Referring to FIG. 1, there is illustrated diagrammatically a specific form of alkylation process for the purpose of illustrating the use of the present invention. In operation, a large stream of hydrocarbons undergoes alkylation in the presence of an acid catalyst such as sulfuric acid. The fresh isobutane and olefin feed enters Reactors 11 through line 10, along with recycle isobutane from line 12 and acid from line 13. The product exits Reactors 11 through line 14 into acid settlers 15. Spent acid is removed through line 16 and is either recycled through line 17 or sent to a degassifier where gases are removed through line 19 and acid is sent through line 20 into holding tank 21.

The recycle acid in line 17 is comprised of water, mineral acid and acid-soluble hydrocarbons, i.e., red oil. The water content is typically from 1 to 9 weight percent, more usually from 3 to 5 weight percent. The mineral acid concentration is typically from 88 to 95 weight percent, more usually from 88 to 92 weight percent. The acid-soluble hydrocarbon concentration is typically from 5 to 10 weight percent, more usually from 5 to 7 weight percent.

Acid is removed through line 22 and purged through valve 23. Probe 1 is suitably placed in line 22 and a signal can be sent to the Near IR Analyzer 24 which is connected to a computer 25. The Probe 1 signal provides the recycle acid concentration.

Fresh acid enters through line 26 and control valve 27 where it mixes with line 17 recycle acid in line 13. Probe 2 is placed in line 26 and a signal is sent to the Near IR Analyzer 24 which is converted in accordance with this invention to provide a fresh acid concentration. Similarly, Probe 3 is placed in line 13 after the recycle acid is mixed with the fresh acid to produce a signal on Probe 3 which is sent to the Near IR Analyzer 24 and is converted via the appropriate computer program to the concentrations of acid entering Reactors 11.

The acid concentrations obtained from Probes 1, 2 and 3 and flow rates on lines 17, 26 and 16 are fed to a standard comparator or electronic controller 28 which operates control valves 27 and 23 to allow sufficient fresh acid to enter line 13 so that the mixed recycle/fresh acid has the desired concentration at predetermined flow rates entering Reactors 11.

The alkylate from settler 15 is removed through line 29 and enters neutralizer 30. The neutralized product is removed through line 31 and enters deisobutanizer 32 where recycle isobutane is removed overhead through line 12 and alkylate is removed through line 33. The alkylate is distilled in 34 to produce a rerun alkylate which is removed through line 35 and a heavy alkylate which is removed through line 36.

A Probe 4 may suitably be inserted in line 35 and a signal sent to Near IR Analyzer 24. This signal can be processed with appropriate computer programs or mathematical models to determine desired product properties such as octane number.

There are three primary acid streams shown in FIG. 1 which are preferred for monitoring acid strength in the system, although it will be recognized by one skilled in the art of refinery alkylation processes that many alternative monitoring locations are possible. It is preferred in the practice of my invention that the acid stream be a substantially homogenous stream, i.e., substantially free of droplets or bubbles. While some bubbles or droplets can be present in the acid stream, too many bubbles or droplets tend to scatter the incident infrared light interfering with the transmission of the said infrared light for spectral analysis. When fewer bubbles or droplets are present in the acid stream, the degree of light scattering is not severe, and I have seen the best results. That is why Probe 1 has been placed, for illustrative purposes, in FIG. 1 just prior to the acid purge in line 22 to minimize the possibility of an emulsion being present.

Figure 2:
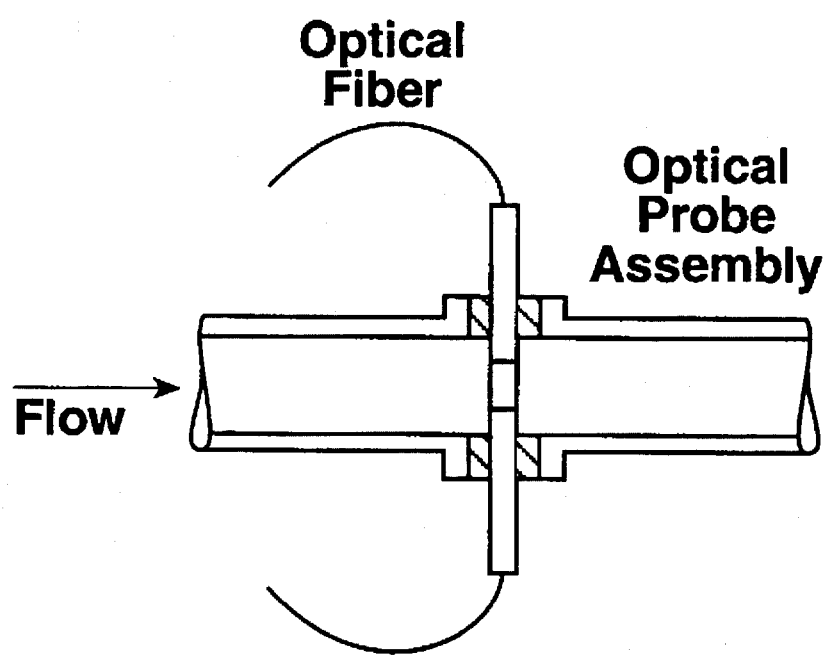
FIG. 2 depicts a cut-away view of the preferred installation of an in-line probe.

FIG. 1 also illustrates the preferred location of a fiber optical probe, the optical waveguide, and the analyzer. The interior of the probe design preferred for my invention is shown in FIG. 2. The design shown in FIG. 2 is useful in making transmission measurements in which the light transmitted through the sample is measured relative to the incident light over the wavelength range used. How to take such transmission measurements is well known in the art.

The preferred probe optical path length for acid-water-red oil analysis is about 2 millimeters. A temperature probe is preferably installed close to the optical probe so that the acid stream temperature is also recorded along with the near-infrared spectra. A temperature correction may be used later in the data analysis to correct the spectra, or alternatively, it is possible in carrying out my invention to use the sample temperature data directly in the multivariate analysis as one of the independent variables.

Near-infrared Spectroscopy

Near-infrared spectroscopy provides chemical information on compounds containing C—H, O—H and N—H bonds. The techniques of near-infrared spectroscopy are described in W. I. Kaye, in The Encyclopedia of Spectroscopy (G. L. Clark, ed.), Reinhold New York, pp. 494–505, 1960, which is fully incorporated by reference herein. For example, according to Weyer (L. G. Weyer, *Applied Spectroscopy Reviews*, Vol. 21 (1 & 2), pp. 1–43, 1985) in the near-infrared wavelength range 700–2500 nm, pure water shows a combination band at about 1960 nanometers, a strong O—H stretch first overtone at 1440–1460 nm, weaker combination bands at 1200 nm, and a weak O—H stretch second overtone at 960 nm.

FIGS. 3a and 3b show absorbance spectra of pure sulfuric acid and water over the range of wavenumbers 4000–7900. FIG. 3a shows the strong absorption band at 5000–5500 wavenumbers for pure water. Pure sulfuric acid does not absorb in this wavelength range as depicted in FIG. 3b. These spectra are again shown in FIGS. 4a and 4c over a narrow range of 4600–5600 wavenumbers. Addition of water to pure sulfuric acid causes absorption of 4395 wavenumber as shown in FIG. 4b. The water absorption band intensity will increase with increasing water concentration. These spectra as shown in FIGS. 4a, 4b, and 4c were recorded on a Mattson Instrument at 2 millimeter path length and room temperature. The results of water addition are further discussed in Example I.

Near-infrared Analyzers

The usefulness of determining solute concentration by measuring its absorbance in the laboratory has been known in the chemical arts. An explanation of the theory and application of NIR is given by Weyer, referenced above, which is fully incorporated by reference herein.

Near-infrared (NIR) spectroscopy is conducted with specialized computerized equipment known as the near-infrared spectrophotometer. There are several suppliers of such equipment including Guided Wave, Inc., El Dorado Hills, Calif.; NIR Systems, Silver Spring, Md.; L. T. Industries, Inc., Rockville, Md.; and Bran & Luebbe Analyzing Technologies, Elmsford, N.Y. The equipment vendors normally supply operating software with their equipment which permits the user to direct their NIR spectrophotometer and to analyze the resulting data. I have utilized such software in the practice of my present invention.

Use of Waveguides/Fiber Optics

An optical fiber is an optical waveguide that carries the infrared light from the analyzer to the sample and the transmitted light back to the analyzer from the sample. Such an optical-fiber device allows on-line measurement of absorption properties from remote locations. Alternatively, the sampling system may include a flow-through cell on a sample bypass loop. The method of measuring chemical composition from spectral analysis is also known as chemometrics. I have used a Guided Wave Model 300 analyzer, which is provided with a jacketed, single-strand, optical waveguide. The optical waveguide has a step index of refraction core made up of doped high-purity synthetic fused silica. This material shows negligible light loss in the near-infrared spectral region 900–1700 nm with light transmission as high as 99.98% transmittance/meter. This high transmittance of silica waveguide allows the use of several hundred meters of cable from the analyzer to the sampling point. FIG. 1 illustrates the use of fiber optics to bring the light to a remote sampling point. FIG. 2 depicts the preferred installation of an optical probe assembly also known as "shuttle probe". The shuttle probe is installed on a process line conducting a process stream of which absorbance data are sought.

Within the 900–1700 nanometer range, there lies a water band at 1380 nm due to hydroxyl absorbance. This absorption band increases with the fiber distance, thereby increasing the light losses and limiting the effective cable length for near-infrared transmission. With increased doping of the core, the water band effect can be substantially reduced.

The Guided Wave Model 300 analyzer I have employed utilizes a single tungsten-halogen lamp as the light source. With the use of appropriate filters, light energy of desired wavelength range passes through a single-strand optical fiber of 500 micron diameter from the analyzer to the sample. I have achieved good results using the 500 micron diameter fiber.

The liquid to be measured absorbs a certain amount of light according to Beer's law. The transmitted light from the sample travels back to the analyzer through a single-strand optical fiber for detection by the analyzer. By comparing the light absorbed by the liquid sample with reference spectra previously taken, I obtain the difference spectrum for the sample over the wavelength range scanned. Throughout the experimental work leading to my present invention, plots were made of the spectra in absorbance units versus wavelength in nanometers. This 900–1700 nm region contains the second overtone and combination bands due to various carbon-hydrogen bonds present in hydrocarbons. Unlike mid-infrared spectroscopy which detects absorbance at fundamental vibrational frequencies, near-infrared spectroscopy detects second and third overtones and combination bands as linear combination of fundamental frequencies. The near-infrared spectrum is quite accurate and highly reproducible.

After the measurements on the Mattson Instrument in the laboratory, the acid-water solutions were run with the same cuvette at a path length of 2 millimeters on the Guided Wave Model 300 Analyzer using a pair of 10-meter optic cables to carry the light to and from the sample. The spectra were in the range 700–1600 nm. See FIGS. 6 and 7 for the spectra recorded on the Guided Wave Model 300 spectrometer using a pair of 10-meter optical waveguides.

The water band, as well as the acid-soluble oil bands, were too strong in this wavelength range. Only the shoulders of these bands could be observed at a path length of 2 millimeters in the spectral range 700–1600 nm. The slope is more sensitive than the peak maximum for reliable analysis. FIG. 6 shows the shoulders of the strong water absorption band for varying amounts of water concentrations in the acid-water solutions.

Analysis of Spectral Data

There are several mathematical techniques for correlating the NIR spectral response to accomplish development of quantitative chemical analyses. They include "Univariate Linear Regression", "Multiple Linear Regression", "Component Spectrum Reconstruction", and "Discriminant Analysis" methods explained in an article by W. R. Hruschka on pages 35–55 of "Near Infrared Technology in the Agricultural and Food Industries", P. C. Williams et al., Editors, American Association of Cereal Chemists, Inc., St. Paul, Minn., 1987 ("Williams"). Other techniques include, for example, "Hruschka Regression", "Fourier Transform Regression", "Principal Component Regression", and "Partial Least Squares Regression" methods explained in detail in an article by H. Martens et al. on pages 57–87 of Williams.

In Chapter 3 of a treatise, "Multivariate Calibration", John Wiley & Sons, Ltd., Chichester, U.K., 1989, H. Martens et al., teach regression techniques including "Univariate Calibration", "Bilinear Modelling", "Self Deconvolution", "Target Transformation Factor Analysis", "Rank Annihilation Method", "Stepwise Multiple Linear Regression", "Ridge Regression", Nonlinear Regression", and "Nonparametric Regression". The "Neural Network" technique explained by D. E. Rumelhart et al. in "Parallel Distributed Processing—Explorations in the Microconstruction of Cognition", Vol. 1, "Foundations" 1986; Vol. 2, "Psychological and Biological Models", 1986; and Vol. 3, "A Handbook of Models, Programs, and Exercises", 1988, MIT Press, Cambridge, Mass., may also be used in the analysis of spectral data.

Although it is possible for a mathematician, scientist, or engineer to generate predictive equations for calculating concentration or physical properties from NIR spectral scans of samples by applying any or several of the above mathematical techniques, either manually or by employing self-contained computer programs, it usually is preferred to employ commercial computer software programs supplied by manufacturers of the near-infrared spectroscopy equipment. These programs provide data storage and retrieval, as well as various data regression and report capabilities directly suited to the development of predictive equations from near-infrared spectral responses. Some commercially available software packages include, for example, "Near-Infrared Spectral Analysis Software" (NSAS) by NIR Systems, Inc., Silver Spring, Md.; "Unscrambler" by Camo A/S Trondheim, Norway; "SpectraMetrix", "LightCal", and "LightCal Plus" by L. T. Industries, Inc., Rockville, Md.; "SpectraCalc" by Galactic Industries Corporation, Salem, N.H.; and "InfraAnalyzer Data Analysis System" (IDAS) and "Principal Component Analysis Program" (PCA-pc) by Bran & Luebbe Analyzing Technologies, Inc., Elmsford, N.Y., and "Pirouette" by Infometrix.

The correlation technique called Partial Least Squares was used in the preferred embodiment of my invention to determine the relationship between the near-infrared spectra and the water content.

The preferred procedure for generating the acid concentration predictive equation uses the Partial Least Squares Regression (PLS) algorithms contained in the "Unscrambler" software. Using these mathematical techniques, the computer can use NIR data to determine concentration of any component in the source streams.

Partial Least Squares

Partial Least Squares ("PLS") regression is a powerful statistical correlation technique for multivariate calibration and prediction. Several PLS algorithms are available for the user; for example, Infometrix's Pirouette and the PLS algorithm developed by the Center for Process Analytical Chemistry (CPAC) in Seattle, Wash.

A general PLS algorithm is described in Geladi and B. R. Kowalski, "*Partial Least-Squares Regression: A Tutorial*", Analytica Chimica Acta, Vol. 185 (1986) 1–17, and in K. R. Beebe and B. R. Kowalski, "*An Introduction to Multivariate Calibration and Analysis*", Analytical Chemistry, Vol. 59, No. 17, Sep. 1, 1987, pp. 1007A–1017A, and in H. Martens and T. Naes, "*Multivariate Calibration*", John Wiley & Sons, New York, 1989, the PLS description of which are fully incorporated by reference herein.

The software known as "Unscrambler" incorporates Partial Least Squares and is licensed from CAMO in Norway. I have found the Unscrambler software particularly useful in the practice of the present invention.

PLS models the near-infrared spectra and associated values for the property of interest, which in the present invention is water content in acid, to find a series of "factors" that describes the relationship between the spectrum and the property of interest.

The data set is the set of "known variables" used to define the model. An individual factor is one phenomenon that occurred in the data set relating the independent spectral responses or X data, to the dependent variable or Y data and vice-versa. In mathematical terms, a factor is defined as any linear combination of the original variables in the measured spectral data or the known variables. Factors are also known as "latent variables", "eigen vectors" or "PLS components".

For the practice of my invention, I have found the process of reducing several independent or spectral variables to a few number of factors as linear combinations of the independent variables eliminates collinearity problems normally encountered in spectroscopy. Collinearity gives rise to an unstable solution.

Model Building

The model may be used for prediction in one of two ways. The short prediction involves translating the model into a set of coefficients (B) which are used in an equation such as:

$$Y = b_1 * x_1 + b_2 * x_2 + b_3 * x_3 + b_m * x_m + b_0$$

where m is equal to the total number of wavelengths in the near-infrared spectrum.

More specific to the preferred embodiment of the present invention, steps involved in developing a model by Partial Least Squares are as follows. First, record near-infrared spectra of the samples over the desired concentration range. Secondly, select a set of training samples which includes as much variation as possible. Sometimes, it may be desirable to select a spectral range which pertains to the concentration or the property being measured.

The practice of my present invention is further described in the examples below, which are intended to exemplify embodiments and are not intended to limit the claims of my invention in any way.

EXAMPLE I

Several sulfuric acid-water solutions were prepared as shown in Table I by mixing a standard sulfuric acid stock solution with oleum and by diluting the same standard stock solution with distilled, deionized water. The acidities of these solutions were determined potentiometrically using a Brinkman automatic acid-base titrator with sodium hydroxide. The acid-water solutions were carefully protected to prevent moisture absorption.

A set of near-infrared spectra were taken at room temperature using a Mattson Instruments Model Cygnus 100 spectrophotometer. A cuvette of 2 millimeter path length was used throughout. FIGS. 3a and 3b compare the near-infrared spectra of pure water and the fuming sulfuric acid respectively. It is noted that the water absorption bands at 6885 and 5178 wavenumbers are absent in the fuming acid spectra. It is important to record the spectra in duplicate by repeating the measurement twice. It may require removing the cuvette containing the sample, removing the sample and refilling after proper cleaning or using a fresh sample in the same cuvette.

Referring to FIGS. 4a–4c, as water was added to the fuming sulfuric acid, the absorption bands due to water start to appear in the acid spectra as shown in FIG. 4b. As the water content increases, the infrared absorption band due to water also increases. Table I details the relationship with water content.

TABLE I

Absorbance Peak Frequency and Peak Areas for Water-Sulfuric Acid Solutions in the 5400–4670 Wavenumber Range

| | Sample | Wt % Water | Band Peak Waveno.* | Peak Area |
|---|---|---|---|---|
| 4 (a) | Fuming sulfuric acid | 0.0 | — | 0.0 |
| (b) | 100.5 wt % sulfuric acid | 0.0 | 4970 | 0.294 |
| (c) | 99 wt % sulfuric acid | 1.0 | 4385 | 0.412 |
| (d) | 98 wt % sulfuric acid | 2.0 | 4458 | 0.477 |
| (e) | 96.6 wt % sulfuric acid | 3.4 | 4774 | 0.449 |
| (f) | 94.4 wt % sulfuric acid | 5.6 | 4473 | 0.609 |
| (g) | 92.4 wt % sulfuric acid | 7.4 | 4540 | 0.649 |
| (h) | 90.3 wt % sulfuric acid | 9.7 | 4559 | 0.705 |

* Wavenumber is the reciprocal of wavelength in centimeters. Wavenumber equals $10^7$ divided by the wavelength in nanometers (nm).

Since the band is quite broad, it was difficult to determine the peak maximum. However, the absorbance unit value at 4950 wavenumber for all samples plotted in FIG. 5 shows a linear relationship between the water content of the acid and the infrared absorption at 4950 wavenumbers.

Since it was difficult to locate the frequency for maximum absorbance, the peak areas between 5400–4670 wavenumbers were also calculated as shown in Table I. A linear relationship appeared to be valid. The acid strength values for the samples were determined by titration and the water content was obtained by difference.

EXAMPLE II

Alkylation Plant Acid Analysis

As described earlier, spent alkylation acid contains not only water but also acid-soluble oil as a third component. In order for this near-infrared analysis to be commercially useful, one needs to know whether the water content of the spent acid can be determined in the presence of acid-soluble oil. The following procedure was used to check the feasibility of using a single spectral measurement to determine both water and the oil present in the acid catalyst.

A sample of the spent alkylation acid was collected from a commercial plant. The acid strength of the sample was determined by titration. Special precaution was taken during titration to eliminate the influence of the acid-soluble oil and the evolution of light hydrocarbons during sample preparation. The acid-soluble oil was first extracted out of the acid phase and then the acid-free oil was added to the acid-water solutions to simulate typical spent acid. The amount of oil added to the acid solutions was small so that the entire amount dissolved completely in the acid solution and separation of a free oil phase was not observed.

The oil was extracted from the acid as follows. The acid sample was first diluted to 50:1 with distilled water. At this dilution, the oil becomes insoluble in the aqueous phase. The diluted acid solution was mixed with an equal volume of chloroform. The resulting two-phase mixture was shaken well and the organic phase containing the oil was separated from the aqueous phase and saved. The extraction step was repeated four times with chloroform to recover as much oil from the acid as possible. The separate organic phases collected from the four extraction stages were combined and the resulting solution boiled at 80° C. to drive the chloroform out and to recover the acid-soluble oil as chloroform-free material. The amount of oil recovered from the acid was then weighed and checked with the original spent acid weight for material balance.

To simulate typical spent acid present in an alkylation plant, a small amount of the extracted oil was added to the acid-water solutions. The amount of oil added was so small that it dissolved completely in the solution. The oil phase did not separate into a second phase over the range of concentrations studied. The 2 millimeter cuvette was again used to record the spectra on the Guided Wave Model 300 analyzer using the optical fibers. Compared to the acid-water spectra as shown in FIG. 8, the samples containing oil showed another shoulder in the 700–1000 nanometer range in addition to the shoulder due to water in the 1300–1550 nanometer previously observed. The figure also depicts the increases in the water absorption band with increasing water content of the spent acid in the presence of the acid-soluble oil. The figure further depicts the increases in the hydrocarbon absorption on the left hand side of the spectrum as the aso content of the spent acid increases in the presence of water. The effect of aso in the presence of water is further demonstrated in FIG. 9. At about 3.5 wt. % water, the effect of increasing aso content from zero to 6.27 wt. % is shown.

Sulfuric acid standards were prepared with varying water content ranging from 0% to 9.7 wt. % water. The standard acid-water solutions were essentially free of process hydrocarbon, and their infrared spectra are shown in FIGS. 6 and 7.

The procedure used to analyze the acid-soluble oil containing samples was similar to that used for the spent acid above, and the measured water content using the near-infrared absorbance data were recorded. To my surprise, it was found the presence of acid-soluble oil in the acid-water standard solutions does not significantly influence the water band of the near-infrared spectrum. The influence of increasing water content in the spent acid is illustrated in FIG. 8 for nearly constant aso content of about 2 wt. %. The influence of increasing aso content from zero to 6.3 wt. % in the spent acid at nearly constant water content of about 3.6 wt. % is illustrated in FIG. 9.

EXAMPLE III

Later, a spent acid sample from a commercial alkylation unit was analyzed using an L. T. Industries near-infrared analyzer model Quantum 1200. The sample was scanned in the range of 900 to 1800 nm wavelength. The water band at 1460 nm was monitored and the absorbance measured using a 1 millimeter path length cell. It is possible to get similar spectral information on the spent acid samples using other commercially available near-infrared analyzers and incorporating either multiple or single fiber optical waveguides. Since the data analysis software supplied by L. T. Industries can be used to perform the multivariate PLS analysis, as explained above in the description of my method, and arrive at the same modeling results, I have omitted the spectral analysis and modeling by the L. T. Industries analyzer.

EXAMPLE IV

The Acid-Soluble Oil Data

However, in the case of acid-water solutions containing the acid-soluble oil, one needs more than a single factor to describe all the effects. For the entire set of samples scanned with the 2 millimeter path length cuvette, the concentration values are shown in Table II.

TABLE II

SULFURIC ACID-WATER-ASO SOLUTIONS
USED FOR METHOD DEVELOPMENT

| | CONCENTRATION IN WEIGHT PERCENT | | |
|---|---|---|---|
| SAMPLE NO. | SULFURIC ACID | WATER | ACID-SOLUBLE OIL |
| 1. | 97.7 | 0.0 | 2.30 |
| 2. | 97.5 | 0.185 | 2.315 |
| 3. | 96.3 | 1.47 | 2.23 |
| 4. | 94.5 | 3.53 | 1.97 |
| 5. | 92.4 | 5.49 | 2.11 |
| 6. | 90.5 | 7.24 | 2.26 |
| 7. | 88.9 | 9.23 | 1.87 |
| 8. | 93.2 | 3.48 | 3.32 |
| 9. | 90.4 | 3.33 | 6.27 |

FIGS. 8 and 9 illustrate the effect of acid-soluble oil and that of water on the near-infrared spectra.

In the case of the spent acid containing the acid-soluble oil, the Y data matrix has two concentration columns, one for the water and another for the oil. The spent acid was simulated by adding a constant amount of the extracted oil to the acid-water solutions. These spectra are shown in FIG. 8. FIG. 9 shows the effect of doubling the oil concentration. The effect of oil was determined to apparently shift the left side of the spectrum upward most probably due to the higher absorption by the oil component since the water content of all samples is relatively equivalent.

To validate the model, a fresh sample of the spent acid from the alkylation plant was scanned in a 2 millimeter path length cuvette. The spectra appear to be similar. Water was added to the plant sample and the sample scanned. For PLS modeling, the acid-water solutions containing the acid-soluble oil were selected, excluding the plant acid. The plant acid spectra were used in the validation test of the method.

FIGS. 11 and 12 show the predicted results versus actual concentrations for acid and water, respectively. The acid-soluble oil content is calculated as {100−(acid content)−(water content)} weight percent. The software on Guided Wave Model 300 analyzer allows the display of any two or all three values for the acid, water, and the aso concentrations for the plant operator to see and follow the trend.

EXAMPLE V

Controlling the Alkylation Process

In the alkylation process as typified by FIG. 1, the spent acid is mixed with fresh acid to raise the acidity from 88 to 90 weight percent. There are several locations available for on-line sampling and monitoring of the acid, in practice with my present invention, including spent acid, recycle acid, and fresh acid. In this example, one such location is selected. Other locations will be a matter of choice.

In FIG. 1, the near-infrared is located on the recycle stream just after the fresh acid make-up section. The near-infrared probe in FIG. 2 may be made using special materials of construction such as sapphire, gold-seal, and steel alloys. Several probe configurations and designs are available that allow installation for on-line analysis. The installation must allow safe removal of the probe for cleaning and referencing without shutting down the process line. Several configurations of near-infrared probes are available and installation must allow safe removal.

The on-line continuous prediction of acidity and oil content is done using a software "macro" written in a proprietary computer language called Macrotask available with the Guided Wave Model 300 analyzers. Unscrambler, the commercially available Scanner software, and the Macrotask language all run on an IBM compatible personal computer. A macro activates the analyzer, checks its calibration, records the spectra, preprocesses the spectra including baseline correction and data smoothing, calls the Unscrambler model residing on the personal computer hard disk, makes a prediction and displays the predicted result, plots the data trends on a round-the-clock basis, and transmits the data to the process control computer.

It is also possible to instruct the personal computer to send out an alarm or a message to the operator at the console so that the operator can act immediately in response to upsets and bring the process to the target value. Alternatively, the output from the analyzer may be interfaced with the hydrocarbon conversion process control system, using the herein described method for predicting acid strength as a process variable to be monitored and optimized for an improved hydrocarbon product.

What is claimed is:

1. In a method for determining the concentration of mineral acid, water and acid-soluble hydrocarbons in a mixture containing unknown quantities of said mineral acid, said water, and said acid-soluble hydrocarbons, the improvement consisting essentially of the use of near-infrared spectroscopy:

wherein said spectroscopy comprises measuring the absorbance in the near-infrared spectra from 900 nm to 1100 nm for said acid-soluble hydrocarbon concentration and measuring the absorbance in near-infrared spectra from 1440 nm to 1460 nm for said water concentration.

2. The use according to claim 1 wherein the concentration of mineral acid is determined using multivariate analysis and the near-infrared absorbance data.

3. The use according to claim 2 wherein the near-infrared spectra is from 900 to 1600 nm and the multivariate analysis comprises the use of a Partial Least Squares algorithm.

4. The use according to claim 3 wherein said mixture is a catalytic solution from a hydrocarbon conversion process.

5. The use according to claim 4 wherein the hydrocarbon conversion process is alkylation.

6. The use according to claim 5 wherein the mineral acid is selected from the group consisting of sulfuric acid and hydrofluoric acid.

7. A method of determining the concentration of mineral acid, water and acid-soluble hydrocarbons which consist essentially of:

(a) developing a set of near-infrared absorbance data curves for various concentrations of the mineral acid, water and acid-soluble hydrocarbons;

(b) generating near-infrared absorbance data curve of said mixture, wherein said mixture contains an unknown concentration of said mineral acid; and (c) determining the concentration of said acid using multivariate analysis and the spectroscopic data from steps (a) and (b) above, wherein said analysis comprises analyzing the near-infrared spectra from 900 nm to 1100 nm for said acid-soluble hydrocarbon concentration and analyzing the near-infrared spectra from 1440 nm to 1460 nm for said water concentration.

8. The method according to claim 7 wherein the near-infrared spectra is from 900 to 1600 nm and the multivariate analysis comprises the use of a Partial Least Squares algorithm.

9. The method according to claim 8 wherein said mixture is a catalytic solution from a hydrocarbon conversion process.

10. The method according to claim 9 wherein the hydrocarbon conversion process is alkylation.

11. The method according to claim 10 wherein the mineral acid is selected from the group consisting of sulfuric acid and hydrofluoric acid.

12. A process for controlling the acid strength in an alkylation process consisting essentially of the steps of:

(a) contacting an alkylation process stream with a catalytic solution comprising a mineral acid, water and an acid-soluble hydrocarbon under alkylation conversion conditions;

(b) spectrophotometrically generating absorbance data of the catalytic solution substantially free of alkylate containing unknown concentrations of mineral acid, water and an acid-soluble hydrocarbon in the near-infrared range;

(c) wherein said analysis comprises analyzing the near-infrared spectra from 900 nm to 1100 nm for said acid-soluble hydrocarbon concentration and analyzing the near-infrared spectra from 1440 nm to 1460 nm for said water concentration;

(d) determining the concentration of acid, water and acid-soluble hydrocarbon in the catalytic solution using multivariate analysis and the spectroscopic data from step (b) plus a standard statistically significant set of near-infrared absorbance data curves for various concentrations of the mineral acid, water and acid-soluble hydrocarbon; and (e) adjusting the concentration of the acid in the catalytic solution with fresh acid to a predetermined range.

13. A process in accordance with claim 12 wherein the spectrographic data of the catalyst solution is generated continuously by in-line techniques.

14. A process in accordance with claim 13 wherein the near-infrared spectra used is from 900 to 1600 nm and wherein the range from 90 to 1100 nm is analyzed for acid-soluble hydrocarbon concentration and the range from 1440 to 1460 nm is analyzed for water concentration.

15. A process in accordance with claim 13 wherein said in-line technique comprises a probe or a flow-through cell in a process line containing said catalytic solution substantially free of alkylate and substantially homogenous.

16. A process in accordance with claim 15 wherein the acid is selected from the group consisting of sulfuric acid and hydrofluoric acid.

17. A process in accordance with claim 16 wherein the acid concentration is adjusted by adding oleum to the acid.

18. A process in accordance with claim 17 wherein said alkylation process is the alkylation of an isoparaffin with an olefin.

19. A process according to claim 12 wherein the concentration of mineral acid, water and acid-soluble hydrocarbon in step (b) is from 88 to 95 weight percent, 1 to 9 weight percent, and 5 to 10 weight percent, respectively.

20. A continuous in-line process for improving alkylation unit performance in a refinery consisting essentially of the steps of:

(a) placing a probe within a substantially emulsion free stream comprising water, mineral acid and an acid-soluble hydrocarbon;

(b) passing energy in the near-infrared range through said acid-containing stream;

(c) generating spectral data resulting from absorbance of a portion of the energy in the near-infrared range by the water and acid-soluble hydrocarbon components in the acid-containing stream;

(d) wherein said analysis comprises analyzing the near-infrared spectra from 900 nm to 1100 nm for said acid-soluble hydrocarbon concentration and analyzing the near-infrared spectra from 1440 nm to 1460 nm for said water concentration;

(e) comparing the resulting spectral data to spectral data obtained by passing energy in the near-infrared range through a standard statistically significant set of substantially pure samples of varying concentrations of the acid, water and acid-soluble hydrocarbon; and (f) adjusting acid strength to within a predetermined range based upon said comparison.

* * * * *